United States Patent
Ceze et al.

(10) Patent No.: US 12,009,062 B2
(45) Date of Patent: Jun. 11, 2024

(54) EFFICIENT CLUSTERING OF NOISY POLYNUCLEOTIDE SEQUENCE READS

(71) Applicant: Microsoft Technology Licensing, LLC, Redmond, WA (US)

(72) Inventors: Luis Ceze, Seattle, WA (US); Sergey Yekhanin, Redmond, WA (US); Siena Dumas Ang, Seattle, WA (US); Karin Strauss, Seattle, WA (US); Cyrus Rashtchian, Seattle, WA (US); Ravindran Kannan, Oakland, CA (US); Konstantin Makarychev, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 967 days.

(21) Appl. No.: 16/325,112

(22) PCT Filed: Sep. 25, 2017

(86) PCT No.: PCT/US2017/053147
§ 371 (c)(1),
(2) Date: Feb. 12, 2019

(87) PCT Pub. No.: WO2018/063950
PCT Pub. Date: Apr. 5, 2018

(65) Prior Publication Data
US 2021/0035657 A1    Feb. 4, 2021

Related U.S. Application Data

(60) Provisional application No. 62/402,873, filed on Sep. 30, 2016.

(51) Int. Cl.
G16B 30/10    (2019.01)
G06F 16/28    (2019.01)
(Continued)

(52) U.S. Cl.
CPC .......... G16B 30/10 (2019.02); G06F 16/285 (2019.01); G16B 40/00 (2019.02); *G16B 30/20* (2019.02)

(58) Field of Classification Search
CPC ....... G18B 30/10; G06F 16/285; G16B 40/00; G16B 30/10
(Continued)

(56) References Cited

U.S. PATENT DOCUMENTS 8,847,799 B1    9/2014  Kennedy et al.
2011/0270533 A1  11/2011  Zhang et al.
(Continued)

OTHER PUBLICATIONS

Z Rasheed, H Rangwala, D Barbara: Efficient clustering of metagenomic sequences using locality sensitive hashing—Proceedings of the 2012 SIAM International Conference on Data Mining (SDM), 2012 (Year: 2012).*

(Continued)

*Primary Examiner* — Russell S Negin
*Assistant Examiner* — Guozhen Liu
(74) *Attorney, Agent, or Firm* — Benjamin Keim; Newport IP, LLC

(57) ABSTRACT

A technique for clustering DNA reads from polynucleotide sequencing is described. DNA reads with a level of difference that is likely caused by errors in sequencing are grouped together in the same cluster. DNA reads that represent reads of different DNA molecules are placed in different clusters. The clusters are based on edit distance, which is the number of changes necessary to convert a given DNA read into another. The process of forming clusters may be performed iteratively and may use other types of distance that serve as an approximation for edit distance. Well clustered DNA reads provide a starting point for further analysis.

16 Claims, 5 Drawing Sheets

(51) Int. Cl.
*G16B 40/00* (2019.01)
*G16B 30/20* (2019.01)

(58) Field of Classification Search
USPC .......................................................... 702/19
See application file for complete search history.

(56) References Cited

U.S. PATENT DOCUMENTS

2013/0138358 A1 5/2013 Tang et al.
2016/0203196 A1 7/2016 Schnall-levin et al.

OTHER PUBLICATIONS

Khalid K Alam, Jonathan L Chang, and Donald H Burke: "FASTAptamer: A Bioinformatic Toolkit for High-throughput Sequence Analysis of Combinatorial Selections", Molecular Therapy—Nucleic Acids (2015) 4, e230 (Year: 2015).*

J. Kim, C. Li and X. Xie, "Hobbes3: Dynamic generation of variable-length signatures for efficient approximate subsequence mappings," 2016 IEEE 32nd International Conference on Data Engineering (ICDE), 2016, pp. 169-180, doi: 10.1109/ICDE2016.7498238. Date of Conference: May 16-20, 2016 (Year: 2016).*

Julien Bringer and Hervé Chabanne: Embedding edit distance to enable private keyword search, Human-centric Computing and Information Sciences 2012, 2:2 (Year: 2012).*

Berlin, K., Koren, S., Chin, CS. et al. Assembling large genomes with single-molecule sequencing and locality-sensitive hashing. Nat Biotechnol 33, 623-630 (2015). https://doi.org/10.1038/nbt.3238 (Year: 2015).*

Rob Patro and Carl Kingsford: ("Data-dependent bucketing improves reference-free compression of sequencing reads", Bioinformatics, 31(17), 2015, 2770-2777).*

Rafail Ostrovsky, and Yuval Rabani: ("Low Distortion Embeddings for Edit Distance", Journal of the ACM, vol. 54 Issue 5, Oct. 2007 pp. 23:1-14 https://doi.org/10.1145/1284320.1284322 (Year: 2007).*

Liu, Lin, et al. "Comparison of next-generation sequencing systems." Journal of Biomedicine and biotechnology 2012 (Year: 2012).*

Pareek, Chandra Shekhar, Rafal Smoczynski, and Andrzej Tretyn. "Sequencing technologies and genome sequencing." Journal of applied genetics 52 (2011): 413-435 (Year: 2011).*

Mardis, Elaine R. "Next-generation DNA sequencing methods." Annu. Rev. Genomics Hum. Genet. 9 (2008): 387-402 (Year: 2008).*

Tabatabaei Yazdi, S. M., et al. "A rewritable, random-access DNA-based storage system." Scientific reports 5.1 (2015): 1-10. (Year: 2015).*

Jhaver, "Calculating Edit Distance for Large Sets of StringPairs using MapReduce", Retreived from: https://www.cc.gatech.edu/~sjhaver3/edit_distance.pdf, 2014, 9 Pages.

"International Search Report and Written Opinion Issued in PCT Application No. PCT/US2017/053147", dated Jan. 4, 2018, 11 Pages.

Slaney, et al., "Locality-Sensitive Hashing for Finding Nearest Neighbors", In Proceedings of IEEE Signal Processing Magazine, vol. 24, Issue 2, Mar. 21, 2008, pp. 128-131.

Ullman, et al., "Chapter 3 Finding Similar Items", Published in Book Mining of Massive Datasets, Dec. 30, 2011, pp. 73-130.

"First Office Action and Search Report Issued in Chinese Patent Application No. 201780060694.X", dated Oct. 19, 2022, 15 Pages.

Arram, et al., "Reconfigurable Filtered Acceleration of Short Read Alignment", In Proceedings of International Conference on Field-Programmable Technology, Dec. 9, 2013, pp. 438-441.

Bai, Xue, "Graph clustering algorithm based on three-strand and three-arm DNA models", In Journal of Computer Application and software, vol. 30, Issue 11, Dec. 31, 2013, 3 Pages.

"Notice of Allowance Issued in Chinese Patent Application No. 201780060694.X", dated Mar. 28, 2023, 4 Pages. (MS# 360584-CN-PCT).

* cited by examiner

EFFICIENT CLUSTERING OF NOISY POLYNUCLEOTIDE SEQUENCE READS

CROSS REFERENCE TO RELATED APPLICATIONS

This application is a National Phase and claims priority to PCT Application Ser. No. PCT/US2017/053147, entitled "EFFICIENT CLUSTERING OF NOISY POLYNUCLEOTIDE SEQUENCE READS," filed Sep. 25, 2017, which claims priority to U.S. Provisional Application Ser. No. 62/402,873 entitled "EFFICIENT CLUSTERING OF NOISY POLYNUCLEOTIDE SEQUENCE READS," filed Sep. 30, 2016 which are incorporated herein in their entirety.

BACKGROUND

Sequencing of polynucleotides such as deoxyribose nucleic acid (DNA) produces errors. Polynucleotide sequencers do not read the sequences of nucleotide bases on DNA molecules with 100% accuracy. However, because the sequence of nucleotide bases cannot be directly observed it is difficult to identify when errors are produced by polynucleotide sequencers. Therefore, the correct sequence of a DNA molecule can at best only be inferred from data generated by polynucleotide sequencers. Analysis of output from polynucleotide sequencers can correct some of the errors. Sometimes moderate levels of accuracy for DNA sequences are sufficient. However, in other instances it is desirable to have DNA sequences that are as accurate as possible. Various techniques are available for reducing errors in sequence data. Some techniques involve calibrating or otherwise changing the operation of polynucleotide sequencers. Other techniques involve processing the sequence data generated by polynucleotide sequencers.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

A large number of reads of DNA strands are received from a polynucleotide sequencer and analyzed. Differences between the sequences of the DNA reads may be due to the DNA reads being representations of different DNA strands or due to errors introduced at some point in the sequencing process. DNA reads that represent entirely different DNA strands likely have sequences that are quite different from one another. DNA reads that are all representations of the same starting DNA strand yet differ due to errors, likely have sequences that are fairly similar. The large number of DNA reads received from the polynucleotide sequencer are clustered into groups such that each group should contain only those DNA reads that represent the same original DNA strand. Stated differently, the variation in DNA reads within one cluster should be due only to errors.

The analysis may determine edit distances between the respective reads and group the reads into clusters based on the edit distance. Edit distance measures the minimum number of insertions, deletions, and substitutions necessary to change one DNA read into another. Edit distance may be approximated by other characteristics of the DNA reads. In one implementation, hash values are used to determine the similarity of DNA reads, and thus, they serve as an approximation for an edit distance. There are multiple ways of computing hash values. One way of computing hash values is to generate a binary signature for a DNA read and create a hash from the binary signature and a string of random numbers.

An iterative process may repeatedly analyze the large number of DNA reads using edit distance and/or a distance between hash values. DNA reads with distances below a threshold distance may be grouped together in the same cluster. Some DNA reads that have already been placed into a cluster may be omitted from subsequent iterations thereby reducing the computational expense of subsequent iterations.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
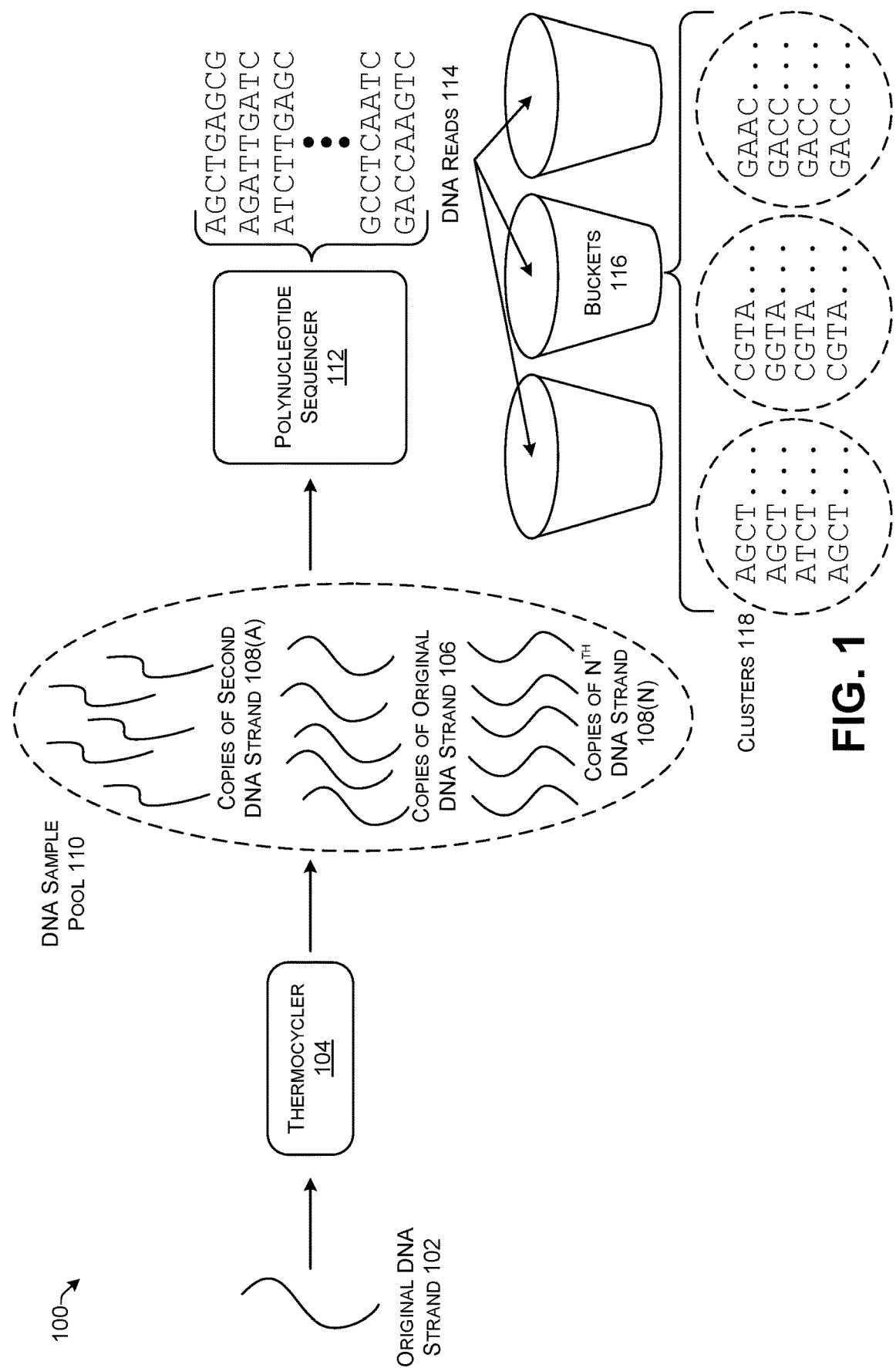
FIG. 1 shows a schematic representation of creating and clustering DNA reads.

This disclosure provides computationally efficient techniques for clustering reads in sequence data so that reads for the same original DNA strand are placed in the same cluster. Clustering reads does not, by itself, correct errors in sequence data but it does organize the DNA reads in a way that makes error correction more efficient and/or accurate. One example of error correction for sequence data that uses clustering is described in US Provisional Patent Application No. 62/329,945. Computational efficiency is desirable for applications involving DNA sequences because of the large volume of data generated by polynucleotide sequencers. For example, the data output by one run of a polynucleotide sequencer may contain over a billion different DNA reads representing millions of different DNA strands.

The term "DNA strands," or simply "strands," refers to DNA molecules. As used herein, "read" may be a noun that refers to a string of data generated by a polynucleotide sequencer when the polynucleotide sequencer reads the sequence of a DNA strand. Reads produced by polynucleotide sequencers frequently contain errors, and thus, do not represent the structure of DNA strands with 100% accuracy. However, DNA sequencing technologies produce multiple reads of a same region of DNA or of multiple different copies of a same DNA strand. The reads are referred to as "noisy reads" because a collection of reads of the same sequence of nucleotides likely contains errors that have an approximately random distribution, i.e. "noise." Although a given read may be error free it is not possible to know which reads are error free or which errors exist unless the sequence is already known. But sequencing is typically unnecessary if the sequence of the DNA strand is already known.

Naturally occurring DNA strands consist of four types of nucleotides: adenine (A), cytosine (C), guanine (G), and thymine (T). A DNA strand, or polynucleotide, is a linear sequence of these nucleotides. The two ends of a DNA strand, referred to as the 5' and 3' ends, are chemically different. DNA sequences are conventionally represented starting with the 5' nucleotide end at the left. The interactions between different strands are predictable based on sequence: two single strands can bind to each other and form a double helix if they are complementary: A in one strand aligns with T in the other, and likewise for C and G. The two strands in a double helix have opposite directionality (5' end attached to the other strand's 3' end), and thus the two sequences are the "reverse complement" of each other. Two strands do not need to be fully complementary to bind to one another. Ribonucleic acid (RNA) has a similar structure to DNA and naturally occurring RNA consists of the four nucleotides A, C, G, and uracil (U) instead of T. Discussions in this disclosure mention only DNA for the sake of brevity and readability, but RNA may be used in place of or in combination with DNA. Additionally, the techniques presented in this disclosure may be readily adapted for DNA or other polymers that contain more or less than four different monomers. For example, DNA that uses a synthetic base together with A, C, G, and T will have an alphabet of five different letters. Moreover, other polymers besides DNA or RNA that are able to be amplified and sequenced in an analogous manner may also be used with the techniques disclosed herein.

Given the convention of representing DNA nucleotides with the letters A, C, G, and T, the reads generated by DNA sequencers are text strings that comprise the letters A, C, G, and T. Some reads may include metadata describing characteristics of the read such as a confidence level for the accuracy of individual base calls in the read. Reads may also contain other letters representing uncertainty in a base call, for example, the letter N may represent an unknown base call.

FIG. 1 shows a schematic representation 100 of creating and clustering DNA reads 114. An original DNA strand 102 represents a single molecule that is to be sequenced. The DNA strand 102 may be extracted from a biological sample, chemically synthesized, or come from another source.

The original DNA strand 102 is amplified to make a large number of identical copies of the DNA strand. A common machine for amplifying DNA strands is a thermocycler 104. Although a thermocycler 104 is described herein, any other technique for amplifying DNA strands may be substituted. The thermocycler 104 (also known as a thermal cycler, PCR machine, or DNA amplifier) may be implemented with a thermal block that has holes where tubes holding the amplification reaction mixtures can be inserted. The term "amplification reaction mixture" refers to an aqueous solution comprising the various reagents used to amplify a target nucleic acid. The thermocycler 104 may then raise and lower the temperature of the block in discrete, pre-programmed steps. Another implementation is a miniaturized thermocycler in which the amplification reaction mixture moves via a channel through hot and cold zones on a microfluidic chip. The behavior and use of thermocyclers including various modifications of the technology is well known to those having ordinary skill in the art. The thermocycler 104 is used for amplifying the original DNA strand 102 by polymerase chain reaction (PCR). PCR is a method for amplifying the concentration of selected sequences of DNA. The term "amplifying" which typically refers to an "exponential" increase in the number of copies of the target nucleic acid is used herein to describe both linear and exponential increases in the numbers of a select target sequence of nucleic acid.

A PCR reaction has three main components: the template, sequencing primers, and enzymes. The template is a single- or double-stranded molecule containing the (sub)sequence that will be amplified. The DNA sequencing primers are short synthetic strands that define the beginning and end of the region to be amplified. The enzymes include polymerases and thermostable polymerases such as DNA polymerase, RNA polymerase and reverse transcriptase. The enzymes create double-stranded DNA from a single-stranded template by "filling in" complementary nucleotides one by one through addition of nucleoside triphosphates, starting from a primer bound to that template. PCR happens in "cycles," each of which doubles the number of templates in a solution. The process can be repeated until the desired number of copies is created.

A variety of PCR techniques are known and can be used in the assays described herein. PCR techniques are typically used for the amplification of at least a portion of a polynucleotide. The sample to be amplified is contacted with the first and second oligonucleotide primers; a nucleic acid polymerase; and nucleotide triphosphates corresponding to the nucleotides to be added during PCR. The natural base nucleotide triphosphates include dATP, dCTP, dGTP, dTTP, and dUTP. Nucleoside triphosphates of non-standard bases can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I and the HIV-1 polymerase.

An additional type of PCR is Droplet Digital™ PCR (ddPCR™) (Bio-Rad Laboratories, Hercules, CA). ddPCR technology uses a combination of microfluidics and surfactant chemistry to divide PCR samples into water-in-oil droplets. The droplets support PCR amplification of the target template molecules they contain and use reagents and workflows similar to those used for most standard Taqman probe-based assays. Following PCR, each droplet is analyzed or read in a flow cytometer to determine the fraction of PCR-positive droplets in the original sample. These data are then analyzed using Poisson statistics to determine the target concentration in the original sample. See Bio-Rad Droplet Digital™ (ddPCR™) PCR Technology.

While ddPCR™ is one PCR approach, other sample partition PCR methods based on the same underlying principles may also be used. The partitioned nucleic acids of a sample can be amplified by any suitable PCR methodology that can be practiced within sample partition digital PCR. Illustrative PCR types include allele-specific PCR, assembly PCR, asymmetric PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, single-cell PCR, solid-phase PCR, thermal asymmetric interlaced PCR, touchdown PCR, universal fast walking PCR, etc. Ligase chain reaction (LCR) may also be used.

Amplification by the thermocycler 104 creates a number of copies of the original DNA strand 106 while also retaining the original DNA strand 102 itself. Any number of copies may be produced. The number of copies is based in part on a number of cycles of amplification. In some implementations around 10-20 copies may be created. All of the copies of the original DNA strand 106 have the same nucleotide sequence as the original DNA strand 102 except for any errors introduced by the PCR amplification process. PCR amplification can cause sequencing errors due to misincorporation of nucleotides by DNA polymerase. PCR is a technique that involves many (often 20-30) rounds of a reaction to synthesize new copies of DNA. The errors that occur during PCR can occur during any round of the DNA synthesis reaction, so a PCR error can result in a large number of DNA fragments with a given error if the polymerase misincorporates a base during an early round of synthesis, or can result in a small number of DNA fragments with errors if the polymerase misincorporates a base a later round of synthesis. Various PCR techniques have been reported as having error rates ranging from $2.4 \times 10^{-6}$ (1:416,667) to $5.6 \times 10^{-5}$ (1:17,857). Paul McInerney, et al., *Error Rate Comparison During Polymerase Chain Reaction by DNA Polymerase*, Molecular Biology Int'l., Article ID 287430 (2014). Thus, on average in a set of one billion DNA strands there will be at most about 55,000 strands with errors introduced through PCR. This level of error is much lower than the error introduced by sequencing. The PCR-induced errors are generally distributed uniformly and randomly and therefore do not introduce bias that would alter the results of the clustering described herein.

Copies of a second DNA strand 108(A) through to any number "N" of other DNA strands 108(N) may be combined with the copies of the original DNA strand 102 prior to sequencing. In some implementations there may be multiple copies of about one million different DNA strands. The combination of multiple copies of multiple different DNA strands is referred to herein as a DNA sample pool 110. The DNA sample pool 110 thus contains multiple, largely identical copies of many different DNA strands. Each of the original DNA strands may be quite different or somewhat similar from each other. The differences between original DNA strands depends on the sequences of the sources of DNA. Assuming, for example, one million different original DNA strands, creation of 20 copies each through amplification, and no errors due to amplification, the DNA sample pool 110 will contain 20 million DNA strands with 20 copies of each original DNA strand. The DNA strands in the DNA sample pool 110 may be mixed and undifferentiated.

The DNA sample pool 110 is provided to a polynucleotide sequencer 112 to determine a sequence of the nucleotides present in the DNA strands within the DNA sample pool 110. The polynucleotide sequencer 112 reads the order of the DNA bases in a given DNA molecule. DNA sequencing includes any method or technology that is used to determine the order of the four bases—A, G, C, and T—in a strand of DNA. Polynucleotide sequencers 112 use a variety of techniques to interpret molecular information, and may introduce errors into read data in both systematic and random ways. Illustrative sequencing technologies are described below. Errors from sequencing are introduced at rates of a few percent to several tens of percent. This is several orders of magnitude greater than errors from PCR. Errors may include, for example, misincorporation of a labelled molecule, such as the fluorescent label used for sequencing by synthesis or the metallic label used for sequencing by electron microscopy. Additionally, if the output data collected during synthesis is of poor quality, nucleotide bases can be misidentified. For example, during sequencing by synthesis the emission peak during fluorescent imaging may be low resolution, or during ion-sensitive field effect transistor (ISFET) sequencing the hydrogen emission peaks may be poorly resolved.

Errors can usually be categorized as substitution errors, where the actual nucleotide is misdetected as another nucleotide (for example A instead of G), insertions where a nucleotide is detected when none exists (for example AGT is read as AGCT), or deletions where a nucleotide is omitted from a read (for example AGTA is read as ATA). Each position in a read is an individual base call determined by the polynucleotide sequencer 112 based on properties sensed by components of the polynucleotide sequencer 112. The properties sensed by the polynucleotide sequencer 112 vary depending on the specific sequencing technology used. A base call represents a determination of which of the four nucleotide bases—A, G, C, and T (or U)—in a strand of DNA (or RNA) is present at a given position in the strand. Sometimes the base calls are wrong and this is a source of error introduced by sequencing.

The polynucleotide sequencer 112 provides raw sequence data output referred to herein as DNA reads 114 (or reads) that contain noise introduced in part by the polynucleotide sequencer 112. The DNA reads 114 may be of approximately the same length (e.g., all close to 100 nucleotides or all between 95 and 105 nucleotides). Returning to the earlier example, if 20 million DNA strands represent 20 copies of a million different DNA strands, the polynucleotide sequencer 112 will sequence 20 million different molecules, and the output will be 20 million text strings (i.e., reads) made up of As, Gs, Cs, and Ts. Thus, to cluster the 20 million reads, a million clusters each containing the 20 reads from the same original DNA strand 102 must be created. This problem is computationally challenging due to the sheer volume of data.

The problem is made more challenging because otherwise identical reads have different sequences due to errors introduced by the polynucleotide sequencer 112 and amplification. However, the data generated by a polynucleotide sequencer 112 reading a DNA sample pool 110 as described above has a unique characteristic. Recognition and appropriate use of this characteristic makes computationally-efficient clustering possible. The DNA reads 114 contain several sets of reads that have sequences which are much more similar to each other than to any of the other reads produced by the polynucleotide sequencer 112. These are the reads that came from the same original DNA strand 102 and the relatively minor differences are those introduced by sequencing or amplification errors. Continuing with the previous example, each set of 20 copies of the same original DNA strand have a much higher similarity to each other than to any of the remainder of the 20 million DNA reads. Of course there is always a possibility that two different original DNA strands may have similar sequences and errors introduced by sequencing may cause a DNA read to appear more similar to other reads that correspond to a different original DNA strand. However, in aggregate and on average, the DNA reads 114 which correspond to the same original DNA strand 102 will be much more similar to each other than to any of the other reads.

In brief, the DNA reads 114 are first separated in a number of relatively large groupings called buckets 116. DNA reads 114 are placed into a same bucket 116 when the DNA reads 114 share a characteristic. Some characteristic that may be used for grouping into buckets 116 include a prefix, address, or hash of the DNA reads 114. DNA reads 114 within each bucket 116 are further grouped into clusters 118. Grouping into a same cluster 118 is based on similarity or "distance" between the sequence of a first read and a second read. Illustrative types of distance that may be used for clustering include Hamming distance and edit distance. Techniques for grouping into buckets 116 and into clusters 118 are described in greater detail below.

The grouping of DNA reads 114 into buckets 116 and clusters 118 is performed iteratively. Each iteration places more of the DNA reads 114 into clusters 118 and regenerates buckets 116. In one implementation, one DNA read 114 for each cluster 118 is designated a representative read, and it is the only read from the cluster 118 analyzed in subsequent iterations. As cluster 118 sizes grow the number of different DNA reads 114 evaluated decreases. This is computationally less expensive than evaluating each DNA read 114 at every iteration. The iterative analysis continues until all reads are sufficiently clustered. The reads may be deemed sufficiently clustered based on a predetermined number of iterations being performed (e.g. 300, 400, 500, etc.). Alternatively, iterations may continue until a characteristic of the clusters satisfies a stopping criteria. For example, suitable stopping criteria include a smallest cluster having at least a minimum number of DNA reads 114 included in the cluster.

Figure 2:
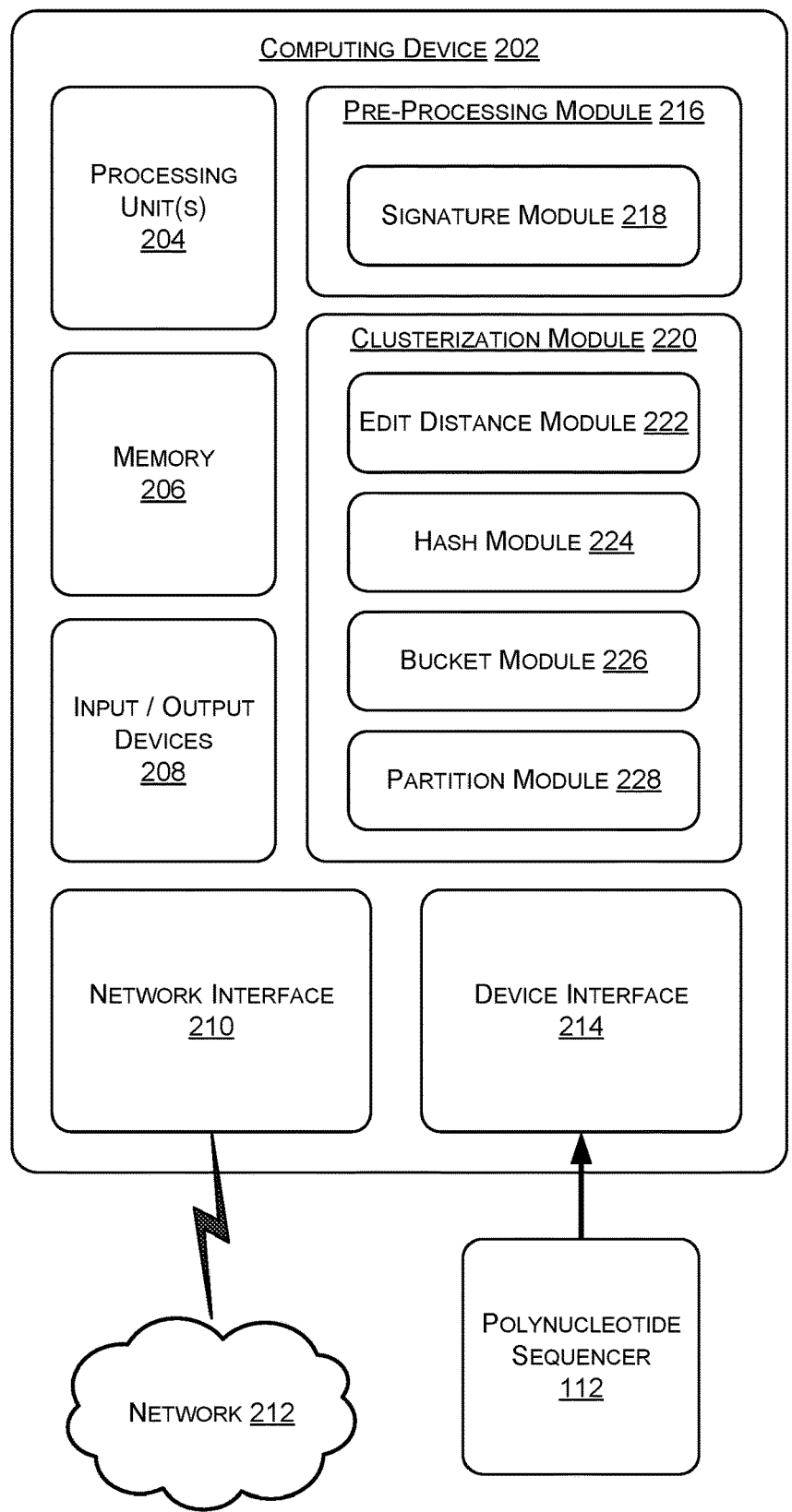
FIG. 2 shows a block diagram of an illustrative computing device.

FIG. 2 shows a block diagram 200 or an illustrative computing device 202 that may be use for forming the buckets 116 and/or clusters 118 introduced in FIG. 1. The computing device 202 may be implemented with one or more processing unit(s) 204 and memory 206, both of which may be distributed across one or more physical or logical locations. The processing unit(s) 204 may include any combination of central processing units (CPUs), graphical processing units (GPUs), single core processors, multi-core processors, processor clusters, application-specific integrated circuits (ASICs), programmable circuits such as Field Programmable Gate Arrays (FPGA), and the like. In one implementation, one or more of the processing units(s) 204 may use Single Instruction Multiple Data (SIMD) or Single Program Multiple Data (SPMD) parallel architectures. For example, the processing unit(s) 204 may include one or more GPUs or CPUs that implement SIMD or SPMD. One or more of the processing unit(s) 204 may be implemented in software and/or firmware in addition to hardware implementations. Software or firmware implementations of the processing unit(s) 204 may include computer- or machine-executable instructions written in any suitable programming language to perform the various functions described. Software implementations of the processing unit(s) 204 may be stored in whole or part in the memory 206.

Alternatively or additionally, the functionality of computing device 202 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Memory 206 of the computing device 202 may include removable storage, non-removable storage, local storage, and/or remote storage to provide storage of computer-readable instructions, data structures, program modules, and other data. The memory 206 may be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer-readable instructions, data structures, program modules, or other data in a modulated data signal, such as a carrier wave, or other transmission mechanism. As defined herein, computer-readable storage media and communications media are mutually exclusive.

The computing device 202 may include one or more input/output devices 208 such as a keyboard, a pointing device, a touchscreen, a microphone, a camera, a display, a speaker, a printer, and the like. Input/output devices 208 that are physically remote from the processing unit(s) 204 and the memory 206 (e.g., the monitor and keyboard of a thin client) are also included within the scope of the input/output devices 208.

A network interface 210 may also be included in the computing device 202. The network interface 210 is a point of interconnection between the computing device 202 and a network 212. The network interface 210 may be implemented in hardware for example as a network interface card (NIC), a network adapter, a LAN adapter or physical network interface. The network interface 210 can be implemented in part in software. The network interface 210 may be implemented as an expansion card or as part of a motherboard. The network interface 210 implements electronic circuitry to communicate using a specific physical layer and data link layer standard such as Ethernet, Infini-Band or Wi-Fi. The network interface 210 may support wired and/or wireless communication. The network interface 210 provides a base for a full network protocol stack, allowing communication among groups of computers on the same local area network (LAN) and large-scale network communications through routable protocols, such as Internet Protocol (IP).

The network 212 may be implemented as any type of communications network such as a local area network, a wide area network, a mesh network, an ad hoc network, a peer-to-peer network, the Internet, a cable network, a telephone network, and the like.

A device interface 214 may be part of the computing device 202 that provides hardware to establish communicative connections to other devices such as the polynucleotide sequencer 112, an oligonucleotide synthesizer, etc. The device interface 214 may also include software that supports the hardware. The device interface 214 may be implemented as a wired or wireless connection which does not cross a network. A wired connection may include one or more wires or cables physically connecting the computing device 202 to another device. The wired connection may be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like. For example, the DNA reads 114 may be received by the computing device 202 via the device interface 214. In some implementations, for example if the polynucleotide sequencer 112 is located remote from the computing device 202, the DNA reads 114 may be transmitted to the computing device 202 via the network 212 and the network interface 210.

The computing device 202 includes multiple modules that may be implemented as instructions stored in the memory 206 for execution by processing unit(s) 204 and/or implemented, in whole or in part, by one or more hardware logic components or firmware.

A pre-processing module 216 performs preprocessing on the DNA reads 114 received from the polynucleotide sequencer 112. The preprocessing may be applied to every read in the plurality of reads received from the polynucleotide sequencer 112. However, in some implementations preprocess may be applied only to a selected subset of the DNA reads 114 that may include all or fewer than all of the plurality of reads received from the polynucleotide sequencer 112. In such instances preprocessing will be applied to all the reads in the selected subset but not necessarily to all of the DNA reads 114 received from the polynucleotide sequencer 112. Reference to "all" or "every" read in the context of clustering refers to the DNA reads 114 included in the selected subset and not necessarily to the totality of reads received from the polynucleotide sequencer 112.

The pre-processing module 216 may create a data structure that contains each of the DNA reads 114 in a separate cluster. The data structure may be a union-find data structure (also called a disjoint-set data structure or merge-find set). A union-find data structure is a data structure that keeps track of a set of elements partitioned into a number of disjoint (nonoverlapping) subsets. It supports two useful operations: "find" and "union." Find determines which subset a particular element is in. Find typically returns an item from the subset that serves as the subset's "representative." By comparing the result of two find operations, the presence of two elements in the same subset can be determined. The clusters 118 of may be considered subsets of the DNA reads 114. Union joins two subsets into a single subset. Merging two clusters into a single cluster is a union operation. Initially a data structure is created that places each DNA read 114 by itself in a cluster 118. Each DNA read 114 is marked as a representative read for the cluster 118 within which it is contained. When there is only one read in each cluster 118, there is only one option for the representative read.

A signature module 218, which may be a part of the pre-processing module 216, computes a signature for each DNA read 114. Signatures are binary representations (i.e., 0s and 1s) of reads. A signature does not uniquely identify a read, but provides a computationally rapid way to identify if two reads are similar or different. For a read X, the signature is represented as s(X). The read X is split in m sub-reads. For example, if the read is 100 nucleotides (nt) long and m=5, then X is split into five sub-reads $X^1$, $X^2$, $X^3$, $X^4$, and $X^5$. The sub-reads may be equal length (e.g., 20 nt) or different lengths. Next, all k-grams are found for a sub-read. For example, if sub-read X="CTAGCAGCA" and k=3 (k may be any integer) then the set of all unique substrings of length 3 includes {CTA, TAG, AGC, GCA}. Repeated substrings are counted only once. In this example the substrings AGC and GCA are counted only once even though each occurs twice. The unique substrings are compared to a comparison string that includes all possible substrings of length k. Given that there are four letters in the DNA "alphabet" the number of possible substrings is $4^k$ which is 64 for k=3. The length of the sub-reads should be less than $4^k$. If the length of a sub-read is longer, the probability of the sub-read containing all or almost all possible substrings of length k increases. Thus, the signature of most all sub-reads would be a string of 1's and it would be difficult to differentiate between sub-reads using the signatures. Continuing with the previous example, the comparison string includes: {AAA, AAG, AAC, AAT, AGA, AGG, AGC, AGT, ACA, ACG, ACC, ACT, ATA, ATG, ATC, ATT, GAA, GAG, GAC, GAT, GGA, GGC, GGG, GGT, GCA, GCG, GCC, GCT, GTA, GTG, GTC, GTT, CAA, CAG, CAC, CAT, CGA, CGG, CGC, CGT, CCA, CCG, CCC, CCT, CTA, CTG, CTC, CTT, TAA, TAG, TAC, TAT, TGA, TGG, TGC, TGT, TCA, TCG, TCC, TCT, TTA, TTG, TTC, TTT}. Each position in the comparison string, that is a match with one of the substrings is represented by 1 and each position in the comparison string that does not have a match is represented by 0 (alternatively 0 may be used to indicate a match). Thus, in this example the binary representation of $X^i$ is a string of length 64 that has four 1s corresponding to the positions where CTA, TAG, AGC, and GCA are found in the comparison string with the remaining 60 positions having a 0. The order of 1s and 0s in the binary representation of $X^i$ of course depends on the order of the substrings in the comparison string. In this example, the binary representation of $X^i$ is {0, 0, 0, 0, 0, 0, 1, 0, 0, 0, 0, 0, 0, 0, 0, 0, 0, 0, 0, 0, 0, 0, 0, 1, 0, 0, 0, 0, 0, 0, 0, 0, 0, 0, 0, 0, 0, 0, 0, 0, 0, 0, 0, 1, 0, 0, 0, 0, 1, 0, 0, 0, 0, 0, 0, 0, 0, 0, 0, 0, 0, 0, 0, 0}. This provides an encoding of the previous k-grams as a bit string.

The full signature s(X) for read X is a concatenation of the bit strings of the sub-reads. Thus, if the number of sub-reads (m) is 5 and the length of k-grams is 3, the length of each bit string is 64, and the total length of the signature (1) is 320. Thus $l=m4^k$.

For signatures calculated in this way, an edit distance (described below) between the reads is small (e.g., less than a threshold T) if and only if the Hamming distance between the signatures of the reads is small (e.g., less than a threshold $T_H$'). The thresholds, both T and $T_H$', may be estimated mathematically to maximize the probability that two reads that are noisy copies of the same original DNA strand end up in the same bucket while keeping the expected size of each bucket small. The estimated thresholds may be adjusted experimentally using a test data set. Signatures are one example a deterministic embedding of edit-distance space into Hamming space. The Hamming distance between two strings of equal length is the number of positions at which the corresponding symbols are different. Hamming distance measures the minimum number of substitutions required to change one string into the other. For binary strings a and b, the Hamming distance is equal to the number of ones (population count) in a XOR b. Signature Hamming distance is usually indicative of edit distance, but exceptions are mathematically possible. Intuitively this relationship can be appreciated because any single change in the sequence of a read affects only a few k-grams in the read's signature.

A clusterization module 220 clusters the DNA reads 114 that have been preprocessed. Clustering is based on a likelihood of the subset of the plurality of reads being derived from a same original DNA strand 102. Although there may be errors in many of the DNA reads 114, reads of copies of the same original DNA strand 102 are generally more similar to each other than they are to reads from a different DNA strand. Further analysis of the DNA sequence data (that is not included in this disclosure), such as correction for errors introduced by polynucleotide sequencing, may be hampered if a cluster of reads includes reads that originated from different DNA strands. Thus, clustering attempts to group those reads that differ only due to errors in sequencing (or PCR) and separate those that come from different DNA strands.

A poorly formed cluster may be "poorly" formed due to over or under inclusion. An overly inclusive, poorly formed cluster is one that groups reads of more than one strand in a single cluster. An under inclusive, poorly formed cluster includes reads that should be grouped into a single large cluster but instead are divided into multiple smaller clusters.

The clusterization module 220 creates clusters based on edit distance between DNA reads 114.

An edit distance module 222 calculates edit distances between pairs of reads. An "edit distance" is equal to the minimum number of insertions, deletions, and substitutions required to transform one DNA read into another DNA read. For example, a first DNA read, X, has the sequence ACGT-TAC and a second DNA read, Y, has the sequence CGTCTAG. The edit distance between read X and read Y, ed(X, Y), is 3. An, illustrative conversion showing the three steps is below.

```
ACGTTAC → CGTTAC (delete first A)

CGTTAC → CGTATAC (add A between the T's)

CGTATAC → CGTATAG (substitute G for the final C)
```

The edit distance between two reads of length L can be computed in time $O(L^2)$ using a standard dynamic programming algorithm such as, for example, the Wagner-Fischer algorithm. Dynamic programming refers to simplifying a complicated problem by breaking it down into simpler sub-problems in a recursive manner. Given the source of the DNA reads 114, the edit distance between any pair of reads will either be relatively small (e.g., less than a threshold distance T) if the pair of reads are both reads of the same original DNA strand 102, or relatively large (e.g., greater than the threshold distance T) if the pair of reads are reads of different DNA strands. Thus, all DNA reads 114 for which the edit distances are less than T may be placed together in the same cluster 118.

In one implementation, edit distances are calculated pair-wise between all of the DNA reads 114 and those groups of reads that have had a distance less than T are grouped together in a cluster 118. However, this approach is computationally expensive because the number of DNA read pairs to be compared grows with the square of the number of the DNA reads 114 to be analyzed. For example, if there are a billion reads to analyze, $1,000,000,000^2$ edit distances must be calculated and this volume of computation may be impractical or prohibitively expensive in terms of computation time. However, other techniques presented in this disclosure can be used to cluster the reads with relatively less computational expense.

A hash module 224 calculates hashes for each representative read. Recall that at the start of clustering, each of the DNA reads 114 is a representative read and each DNA read 114 is in a cluster by itself. In one implementation, the first iteration uses a hash code based on the prefix (e.g., first 1-8 nucleotides) of the DNA reads 114. The hash code may interpret each of the nucleotides as a different number in a four-base system and then convert the nucleotide string into a numeric string. In this implementation, hash codes for later iterations are calculated as described below. In one implementation, hash codes are computed as described below in all iterations. One type of hashing that may be used is randomized locality-sensing hashing (LSH). Hashes may be calculated only for representative reads, so in subsequent iterations, hashes are calculated for less than all of the reads.

In an implementation, hashing begins with generation of a random permutation of numbers (r) the length (l) of the signature. The random permutation is a list of integers from 1 to l that is in random order and includes each integer only once. Thus, $r=(r_1 \ldots, r_l)$, from 1 to l.

The hash is a selection of the numbers from r. Recall that s is a string of 0s with some 1s included. r and s are the same length. In the example below both s and r have 9 positions. The algorithm considers numbers from r one-by-one from $r_1$ to $r_l$: For every i=1 . . . l, it checks whether $s_{r_i}=1$, if $s_{r_i}=1$, then the algorithm adds $r_i$ to the hash. The algorithm terminates when q numbers are added to the hash. The hash for a read X with signature (s) is represented by $h_r(s)$. The hashes may be limited to the first q numbers that correspond to a 1. Thus, $h_r(s)$ is the first q numbers in $r_i$ in r such that $s_{r_i}=1$. If used, q may be any number equal to or less than 1. In some implementations q may be between 7 and 15. For example, if q=2 and $$s=(0,0,1,0,0,1,0,1,0)$$

$$r=(4,7,9,1,8,5,3,2,6)$$

then the positions in r for which the corresponding positions in s=1 are 3, 6, and 8. Each integer in r is checked in numerical order (from left to right: 4, 7, 9, 1, 8, 5, 3, 2, 6) to determine if the corresponding position ins has a 0 or 1. If there is a 1, then the corresponding position in s is added to the hash. In the example above, the number 8 in position 5 in r is the first number that corresponds to a 1 in s (i.e. $s_8=1$). Thus, the first value in the hash is 8—the position in r with the first number that corresponds to a 1 in s. The next lowest number in r that corresponds to a 1 in s is 3 at position 7. When limited to the first 2 numbers, $h_r(s).=(8, 3)$. Given a particular r, reads with the same signature will have the same hash. Recall from the definition of signatures that reads with different base sequences may have the same signature. A decrease in q increases a number of reads that share the same hash code. In the above example, if q=2, then any read with $h_r(s)=(9, 5)$ will share the same hash, but if q=3 then only the reads with $h_r(s)=(9, 5, 2)$ will share the same hash. In some implementations, q may increase in later iterations thereby increasing the specificity of the hashes in later iterations.

The probability over a random choice of r that $h_r(s')=h_r(s'')$ for two signatures s' and s'' is approximately equal to $J(s',s'')^q$, where $J(s',s'')$ is the Jaccard similarity coefficient for s' and s'' defined as follows:

$$J(s', s'') = \frac{\text{\# of } 1s \text{ in}(s' \text{ and } s'')}{\text{\# of } 1s \text{ in}(s' \text{ or } s'')} = \frac{\|s_1\|_1 + \|s_2\|_1 - \|s_1 - s_2\|_1}{\|s_1\|_1 + \|s_2\|_1 + \|s_1 - s_2\|_1}$$

And if s' and s'' are considered subsets of $\{1, \ldots, 1\}$ then:

$$J(s', s'') = \frac{|s' \cap s''|}{|s' \cup s''|}$$

If $s_1=s_2$ then $J(s',s'')=1$. If the Hamming distances between $s_1$ and $s_2$ is small, then $J(s', s'')$ is close to 1. If the Hamming distance between $s_1$ and $s_2$ is large, then $J(s',s'') \ll 1$. If $s_1$ and $s_2$ are disjoint then $J(s',s'')=0$. Hence, for any arbitrary threshold T, the probability that two reads X and Y have the same hash code is much larger for X and Y at edit distance of at most T than for X and Y at edit distance larger than T. Thus, this design of the hash code partitions the Hamming space occupied by the signatures in a way that only a relatively few reads out of all the DNA reads 114 share the same signature and two reads with the same hash are likely to have an edit distance at most T.

In an implementation, the hash for read X may be calculated without using the signature and this type of hash is represented as $h_r(x)$. This hash is a string of q nucleotides following an "anchor" string. The "anchor" string is a random string r of length p. Multiple random "anchor" strings may be independently generated so that there exists a series of "anchor" strings $r_1, \ldots, r_k$ (e.g., k=5). The hash is then set as the string of q nucleotides adjacent (i.e., before or after) the first occurrence of the anchor string r in the read X If the first anchor string $r_1$ is not found in the read, then the second anchor string $r_2$ and each subsequent anchor string is checked until a match is found. For example, if p=3 and if the random selection of nucleotide sequences of length three generates $r_1$="ACG" and X="ACGTACGAC", then, the first occurrence of $r_1$ in X is the first three nucleotides. The next q nucleotides (if q=6) are "TACGAC". Thus, $h_r(x)$ is TACGAC in this example.

At the beginning of each iteration $r=r_1, \ldots, r_k$ may be randomly generated. Then $h_r(x)$ is computed for all the reads using the same r. All buckets 116 created by the bucket module 226 (below) in a previous iteration are sorted in lexical order based on the hash $h_r(x)$ from the previous order used to group the reads into given bucket 116. Then a new "anchor" string for the current iteration (which will likely have a different value due to random generation) is used to compare reads in a given bucket 116 and buckets adjacent in the lexical order. Reads with the same hash are then grouped in new buckets.

The bucket module 226 divides the DNA reads 114 into buckets 116. One technique for generating buckets based on hash values is described above. In each iteration, the representative reads are separated into buckets 116. The number of representative reads decreases as cluster formation progresses (discussed in greater detail below) so the number of items that are considered for each round of bucket 116 creation progressively decreases. In one implementation, all DNA reads 114 with the same hash are placed into the same bucket 116. Bucket size, the number of different reads within a single bucket, may be tuned by selection of q (this is true for both q representing a number of "1's" from a binary string and for q representing the number of nucleotides adjacent to the "anchor" string). In one implementation, bucket size may begin relatively large and then decrease (i.e., have fewer reads in each bucket) as q is increased in subsequent iterations. In one implementation, the bucket module 226 may also remove a cluster 118 from one bucket 116 and merge it with a cluster 118 in another bucket 116. In one implementation, DNA reads 114 are grouped into the same bucket 116 based on prefixes or addresses. The prefixes or addresses are portions of the DNA reads 114 that are likely to be identical if the DNA reads 114 are very similar. In an implementation, the prefixes or addresses may be analyzed as deterministic hash functions. Thus, DNA reads 114 with the same prefix or the same address may be placed in the same bucket 116.

A partition module 228 assigns to DNA reads 114 that are in a same bucket 116 to a same cluster 118 based on an edit distance between the two DNA reads 114 being less than a threshold distance. The edit distance between two DNA reads 114 may be estimated based on the Hamming distance between the signatures of the two DNA reads 114. For the reasons described above, if the Hamming distance between two signatures is small, then the edit distance is also likely to be small. Conversely, if the Hamming distance between two signatures is large, then the edit distance is likely to be large.

The partition module 228 may use Hamming, hDistance, distance between the signature of DNA read X, $s_X$, and the signature of DNA read Y, $s_Y$, to group DNA reads 114 in a same bucket 116 when the Hamming distance is relatively small. Thus, hDistance=$\|s_X - s_Y\|_1$. If hDistance is less than the first threshold value, $T_H'$, then DNA read X and DNA read Y are merged into the same cluster 118. However, if hDistance is greater than a second, larger threshold value, $T_H''$, then DNA read X and DNA read Y are maintained in different clusters 118. The partition module 228 may perform a pairwise comparison between each pair of DNA reads 114 in the bucket 116. The two thresholds, $T_H'$ and $T_H''$, maybe selected experimentally, set by a user, or based on results calibrated from known data sets.

Thus, in this implementation, many DNA reads 114 may be grouped into clusters 118 by using only the signatures. Computing the Hamming distance between two binary strings is less computationally expensive than computing the edit distance, and thus, using signatures instead of edit distances allows for clustering of many DNA reads 114 in an efficient manner. However, for a pair of DNA reads 114 that have Hamming distance between $T_H'$ and $T_H''$, the partition module 228 may use edit distance to determine if the DNA reads 114 are grouped in the same cluster 118 or not. For each of the DNA reads 114 in the same bucket 116 that cannot be placed in a cluster by the use of signatures, the partition module 228 may perform pairwise comparisons of edit distances. The edit distance for DNA read X and DNA read Y, ed(X, Y), is compared to a threshold T, and if ed(X, Y)≤T then DNA read X and DNA read Y are placed in the same cluster 118. Calculating edit distance between DNA reads 114 is more computational expensive than calculating Hamming distance between signatures. By using Hamming distances between signatures as being approximately representative of edit distance, it is possible to reduce the number of edit distance calculations while still clustering the DNA reads 114 with reasonable accuracy.

A consensus output sequence generator determines a single consensus output sequence from a clustered set of reads. The consensus output sequence is a string of data similar to any of the reads, but the consensus output sequence is generated from analysis of the reads rather than being output directly from a polynucleotide sequencer. The process of going from many noisy reads to one, presumably accurate, consensus output sequence is referred to as "trace reconstruction." The consensus output sequence represents the sequence of nucleotides in a DNA strand with less error than any of the individual noisy reads and ideally with no error.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

Binary data of the kind currently used by computers to store text files, audio files, video files, software and the like can be represented as a series of nucleic acids in a polynucleotide (i.e., DNA or RNA). DNA has great potential as a storage media for digital information and may be used to store digital data. Briefly, digital information that is intended for storage as DNA molecules is converted into information representing a string of nucleotides. The information representing the string of nucleotides (i.e., a string of letters representing an order of nucleotide bases) is used as DNA-synthesis templates that instruct an oligonucleotide synthesizer to chemically synthesize a DNA molecule nucleotide by nucleotide. Artificial synthesis of DNA allows for creation of synthetic DNA molecules with arbitrary series of the bases in which individual monomers of the bases are assembled together into a polymer of nucleotides.

In implementations in which the DNA is used to encode digital information, the computing device 202 may include a converter. The converter converts the consensus output sequence into binary data, thereby retrieving the digital information stored in a DNA storage library. The converter may use additional error correction techniques to correct any errors that may remain in the consensus output sequence.

Figure 3:
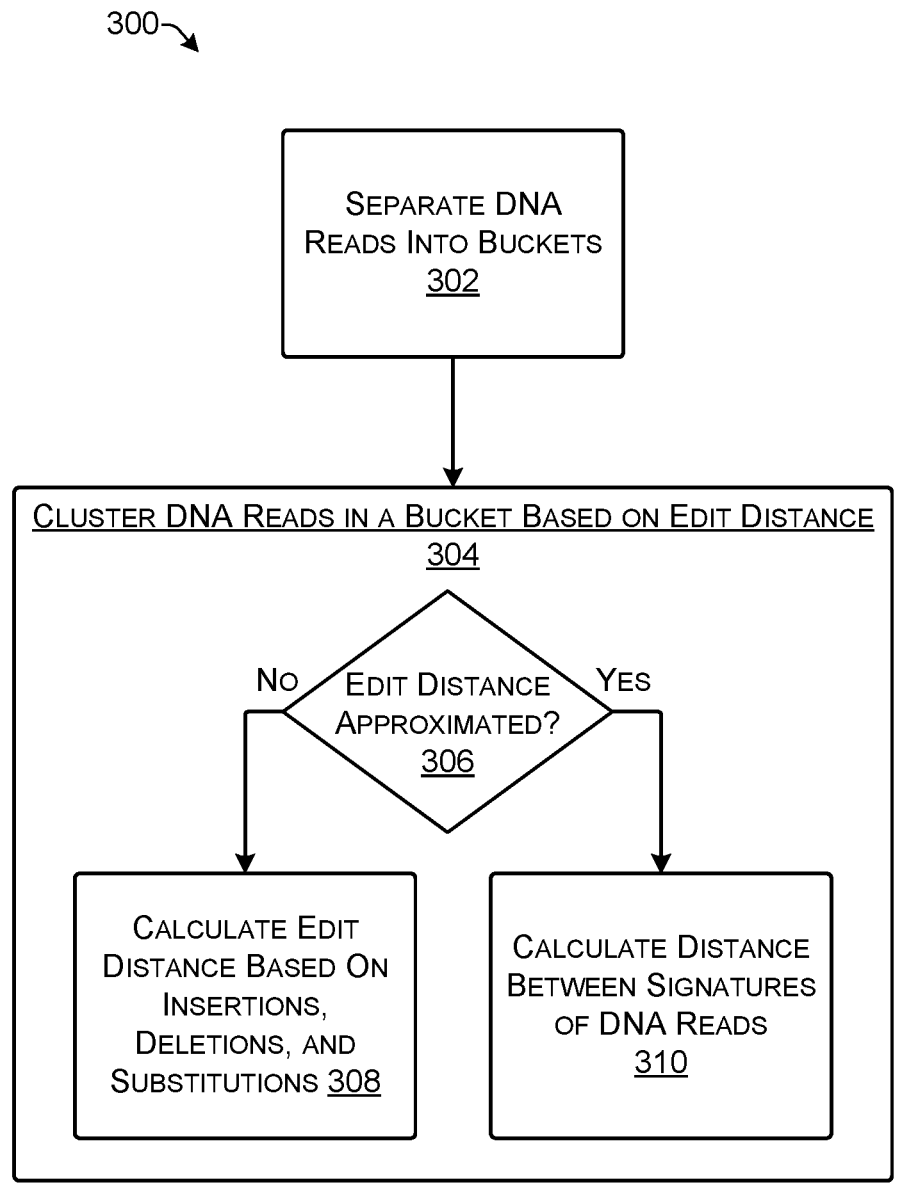
FIG. 3 shows a process of clustering DNA reads.

FIG. 3 shows process 300 for clustering DNA reads. The process 300 may be implemented in whole or part by the computing device 202 shown in FIG. 2.

At 302, a plurality of DNA reads separated into a plurality of buckets. The separation may be performed in part by the bucket module 226. The DNA reads may be separated into buckets based in part on prefixes of the plurality of DNA reads. Thus, DNA reads with the same prefix may be placed in the same bucket. In one implementation, hashes may be generated from the prefixes and DNA reads with the same hash (based on the prefix) may be placed in the same bucket. In one implementation, hashes may be generated from a binary signature of the DNA reads in a random permutation of numbers as described above. In one implementation the hashes may be generated by the "anchor" string and following nucleotides. The DNA reads with the same hash (however generated) may be placed in the same bucket. Thus, every DNA read in a given bucket may have the same hash. All or part of process 300 may be repeated iteratively. The method of placing the DNA reads into buckets may be different in different iterations. For example, the hash values may be based on the prefixes of the DNA reads in one iteration and based on the combination of the signatures and random numbers in different iteration. The random numbers used to generate the hash may be altered in different iterations. The value of q used to generate the hashes may vary between iterations.

At 304, the DNA reads within one of the buckets are clustered based at least in part on edit distance. Clusters may be formed by the clusterization module 220. Because each bucket only contains a portion of the total number of DNA reads received from the polynucleotide sequencer, creation of clusters within a single bucket is computationally less expensive than creating clusters for all of the DNA reads without first making buckets because using buckets limits the number of DNA reads that must be analyzed in each cluster analysis. Using buckets also makes process 300 amenable to implementation on a multicore processing system in which each processor or core receives the task of creating clusters within one bucket.

Within 304, the edit distance may be approximated or calculated. At 306, if the edit distance is not approximated, process 300 proceeds to 308 where the edit distance is calculated by a minimum number of insertions, deletions, and substitutions to transform a first DNA read into a second DNA read. The edit distance may be calculated by the edit distance module 222. Calculating edit distance directly is the most accurate way of determining edit distance, but it may be more computationally expensive than alternative techniques.

If, at 306, the edit distance is approximated then process 300 proceeds to 310. At 310, the edit distance is approximated by a Hamming distance between a binary signature of a first DNA read and a binary signature of a second DNA read. The binary signatures may be calculated by the signature module 218. In some implementations, the binary signatures are pre-calculated so that at this stage in process 300 the binary signatures are retrieved from memory rather than calculated.

Returning to 304, if edit distance is being approximated, the Hamming distance between signatures may be determined to be less than a first threshold Hamming distance and the first DNA read and a second DNA read may then be placed into the same cluster. A Hamming distance between signatures is a reasonable approximation for edit distance in some circumstances for the reasons explained above. Alternatively, the Hamming distance may be determined to be greater than a second threshold distance in which case the first DNA read the second DNA read will be placed into different clusters. If the Hamming distance is more than the first threshold distance but less than the second threshold distance using an approximation for edit distance may be unreliable way to cluster those DNA reads. Thus, DNA reads with Hamming distances in this range, the edit distance may be calculated.

Thus, edit distance may be used if a decision was made to use edit distance instead of an approximation, or alternatively if the approximation is unlikely to be able to accurately cluster a given pair of DNA reads. When edit distance is used, the DNA reads with edit distance less than an edit-distance threshold may be placed into the same cluster. DNA reads with edit distances greater than the edit-distance threshold may be placed into different clusters. The grouping or separating of DNA reads into the same or different clusters may be performed by the partition module 228.

Figure 4A:
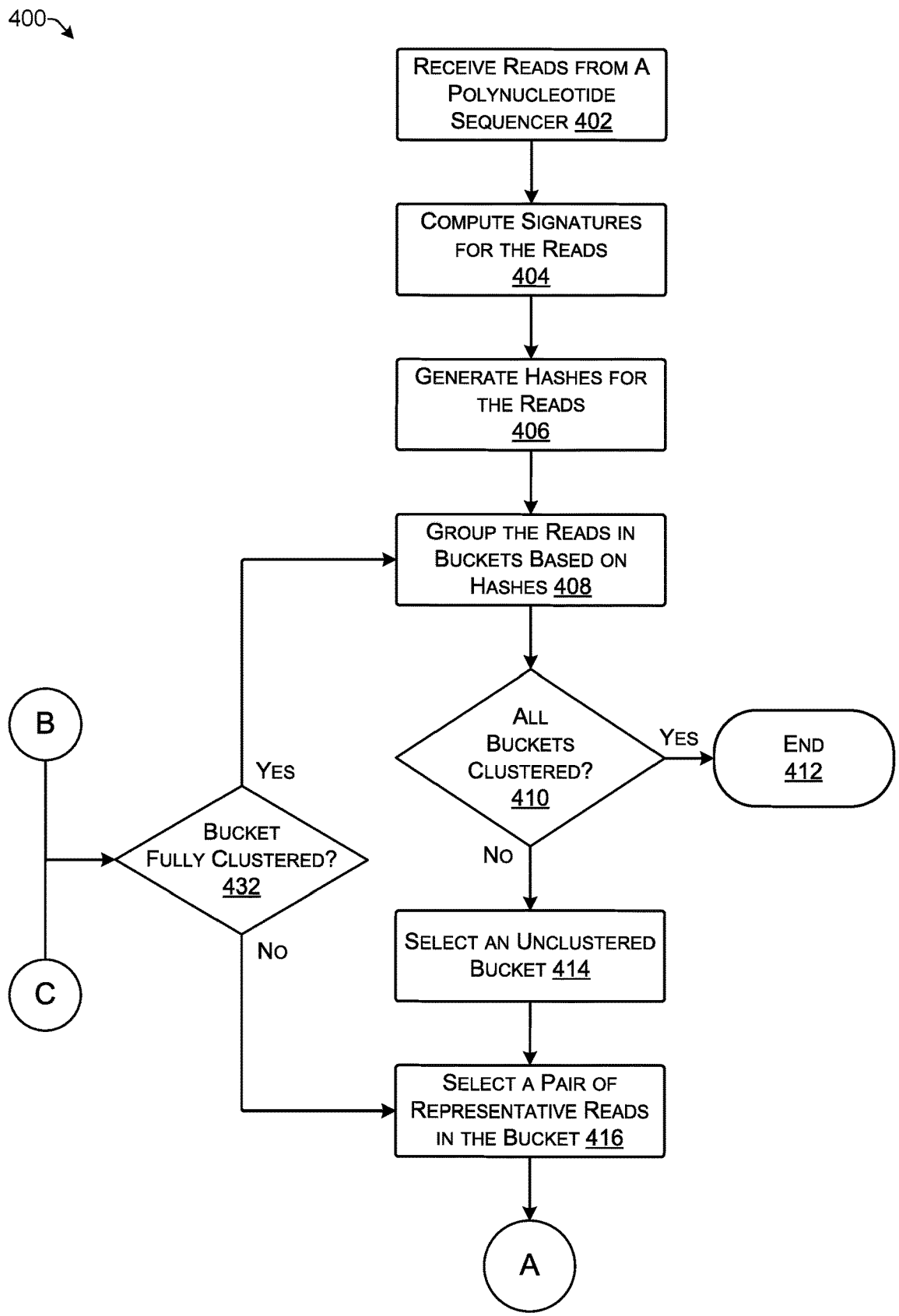
FIGS. 4A and 4B show a process of clustering DNA reads.
Figure 4B:
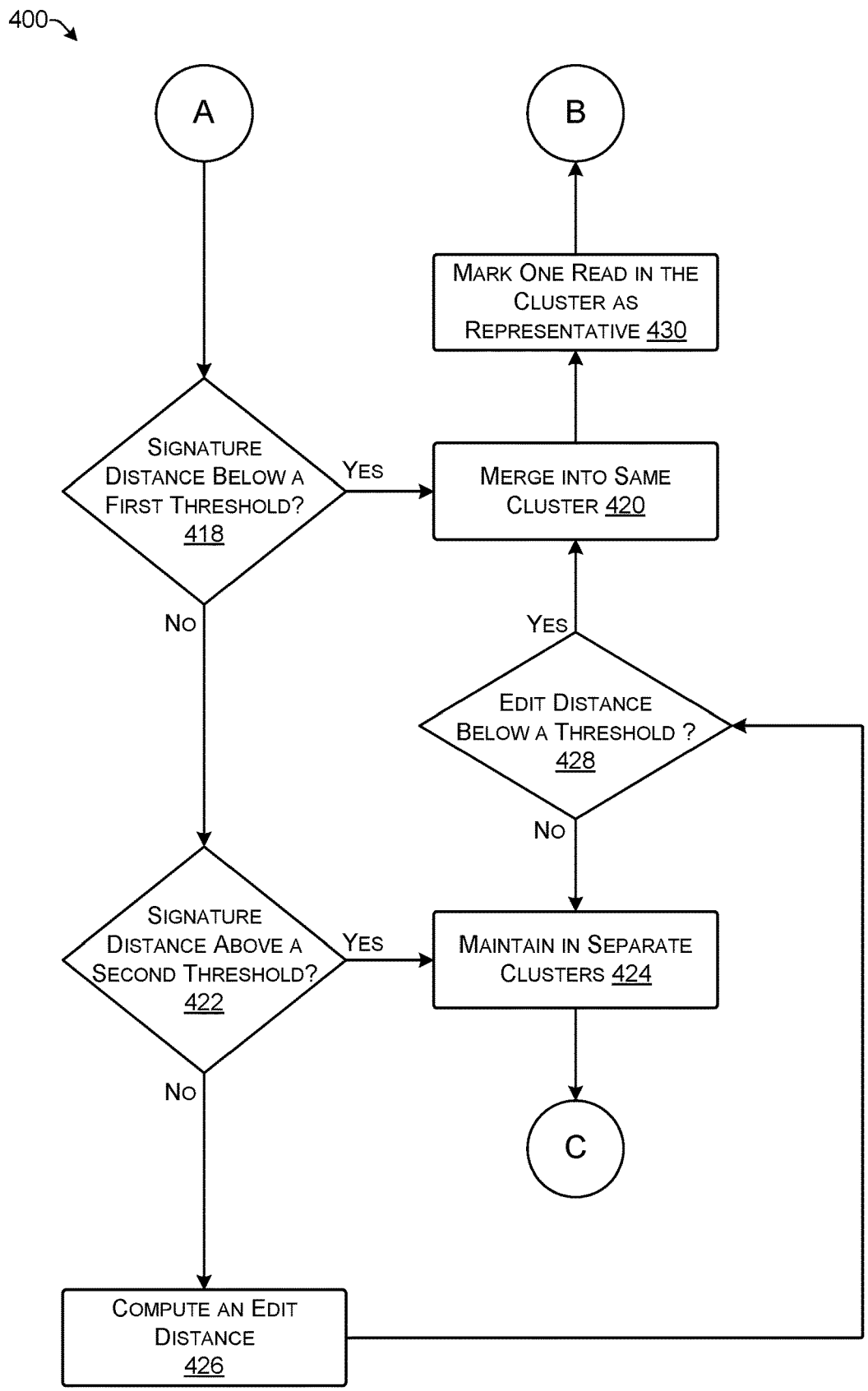

FIGS. 4A and 4B show process 400 for clustering DNA reads. The process 400 may be implemented in whole or part by the computing device 202 shown in FIG. 2.

At 402, plurality of reads received from a polynucleotide sequencer. The polynucleotide sequencer may be the polynucleotide sequencer 112 shown in FIG. 1 and FIG. 2. The plurality of reads is received via the device interface 214. Current sequencing technology may produce a very large number (i.e., 1,000,000,000 or more) of reads from a large number (i.e., 1,000,000 or more) of DNA strands.

At 404, signatures may be computed for at least the first read from the plurality of reads. The signature may be any type of signature, but in one implementation the signature is a bit string generated by a set of k-grams (e.g., 3-grams, 4-grams, 5-grams, etc.) within the first read. The signature may be computed by dividing the first read into two or more sub-reads. For example, the first read may be divided into five sub-reads of equal length. Then all k-grams may be found for each of the sub-reads. The k-grams may be encoded as bit strings using 1 to indicate a k-gram that is present in the substring and 0 to indicate a k-gram is not present (of course the use of 1 and 0 may be switched). This creates bit strings for each of the substrings and these bit strings may be concatenated to create a signature for the first read. The signatures may be created by the signature module 218.

At 406, a hash may be generated for the first read based on any of the techniques described above. For example, the hash may be based at least in part on the signature and a string of random numbers. The string of random numbers may be generated as a random permutation of numbers that contains integers with each integer included only once. A different random number from the string of random numbers is assigned to individual bits in the signature. The individual bits may be selected based on bit value. For example, all the bits of the value 1 maybe selected; alternatively, all the bits of value 0 may be selected. The hash is then set as a subset of the string of random numbers that are assigned to individual bits in the signature. The hash may include all of the numbers that are assigned to individual bits in the signature or only the first several such as the first 2, 3, 4, 5, 6, 7, 8, 9, 10, 11, 12, 13, 14, or, 15 etc. The hash may be generated by the hash module 224. As a further example, the hash may be generated from an "anchor" string and the following q nucleotides. The "anchor" string is k different alternative random strings of length p that, if present in a read, designate where a hash begins. The hash is the string of nucleotides of length q that is adjacent to (i.e., follows or precedes) the "anchor" string. In one implementation p=3, q=8, and k=5.

At 408, the reads may be grouped into buckets based on the hashes. Reads with the same hash value are grouped into the same bucket. The reads may be grouped in buckets by the bucket module 226.

At 410, it is determined if clustering is completed for the read in all of the buckets. Each of the buckets may be analyzed in turn to determine if there is additional clustering that should be performed. Additional clustering may be performed if there are small clusters that contain less than a threshold number of DNA reads (e.g., five or fewer DNA reads). Iterations of clustering may also be repeated a set number of times. The number of times may be determined experimentally based on previous clustering of other sequence data. If no more clustering is needed for any of the buckets, process 400 proceeds to 412 and ends. However, if clustering is not complete for one or more the buckets, process 400 proceeds to 414 and selects a bucket that is not completely clustered for additional clustering.

At 416, a pair of representative reads are selected from the bucket selected at 412. The pair of reads may be selected in any manner such as taking the first two reads in a list of the reads, selecting randomly, etc.

At 418, a signature distance between the selected pair of representative reads is compared to a first signature distance threshold. In one implementation the signature distance may be a Hamming distance. The signature distance may be designed, for example using the techniques described above, so that any two reads with the signature distance below the first signature distance threshold are very likely to have an edit distance that would cause that two representative reads to be placed in the same cluster. If it is determined that the signature distance is below the first signature distance threshold, then process 400 proceeds to 420 and the clusters containing the representative reads are merged into one cluster. If, however, the signature distance is not below the first signature distance threshold, then process 400 proceeds to 422.

At 422, the signature distance between the two representative reads is compared to a second signature distance threshold. A signature distance above the second signature distance threshold indicates a high probability of the two representative reads having an edit distance that would place the two reads in different clusters. If it is determined that the signature distance between the two representative reads is above the second signature distance threshold, process 400 proceeds to 424 and the clusters containing the two representative reads are maintained as separate clusters. If, however, it is determined that the signature distance is less than the second signature distance threshold (and recall that at this point in process 400 the signature distance is also greater than the first signature distance threshold) then process 400 proceeds to 426.

At 426, an edit distance is computed between the selected pair of representative reads. The edit distance may be computed by the edit distance module 222. Because the edit distance is only computed for pairs of reads that have signature distances above the first signature distance threshold and below the second signature distance threshold, it is not necessary to calculate the edit distance for a portion of the reads received from the polynucleotide sequencer. If the reads coming from the polynucleotide sequencer are reads of multiple copies (i.e., differ due to errors) of multiple DNA strands (i.e., differ due to different original sequences) most pairs of reads will either be similar enough that the signature distance is below the first signature distance threshold (e.g., reads that differ only due to errors) or be different enough that the signature distance is above the second signature distance threshold (e.g., reads that are of different DNA strands). Thus, in many implementations edit distance is computed only for a small portion of the reads received from the polynucleotide sequencer. This creates computational efficiencies because signature distance is less computationally expensive to compute than edit distance.

At 428, the edit distance computed at 426 is compared to a threshold value. If the edit distance is above the threshold value, process 400 proceeds to 424 and the two representative reads are maintained in separate clusters. If the edit distance is above the threshold value, process 400 proceeds to 420 and the two reads are merged into the same cluster.

Following a determination at 420 that two reads, and the clusters they represent, should be merged into one cluster, process 400 proceeds to 430 and marks one read in the newly formed cluster as a representative read for that cluster. Each cluster of reads may include one read that is designated as a representative read for the entire cluster. Grouping of multiple different reads in the same cluster is an indication that the sequences of those reads are the same or similar due to the edit distance being less than a threshold value. Recall that in the initial iteration, every read may be by itself in a cluster and every read may be indicated as a representative read. Once multiple different reads are merged together in the same cluster some of those reads, for example all but one, are ignored in further analysis; only the representative reads are considered when evaluating the cluster. The representative read may be selected by any suitable technique. In one implementation, the representative read for a cluster may be selected at random. In one implementation, the representative read may be selected from the representative reads of the clusters that merged. For example, the representative read for a new cluster may be the representative read from the one of the two merged clusters that contained the larger number of reads.

Following the marking of one read as representative at 430 or the determination at 424 that a pair of representative reads are to be maintained in separate clusters, process 400 proceeds to 432.

At 432, it is determined if the currently selected bucket is fully clustered. If not, process 400 returns to 416 and selects a different pair of active reads in the bucket for analysis. As the number of clusters in the selected bucket decreases, the number of active reads will also decrease, so choices for pairs of active reads to compare will decrease. Eventually, all pairs of active reads that may be clustered together will be clustered and then only active reads that are more than the edit distance threshold away from each other will remain.

If, at 432, it is determined that all the reads in the currently selected bucket are fully clustered, then process 400 proceeds to 408 and creates new buckets based on the hashes of the representative reads. Because only representative reads are used in this analysis, forming new buckets does not break up existing clusters, but does provide an opportunity for different combinations of clusters to be placed in a same bucket. Once new buckets are formed, process 400 continues as described above. In some implementations, all or part of process 400 may be iterated 100, 200, 300, 400, 500, 600, 700, 800, or 900 times.

EXAMPLE

The follow example illustrates differences in accuracy and computational expense between multiple ways of clustering DNA reads. All results in this example were computed on a computing device with an Intel® Xeon® CPU, W3670@3.20 GHz, 6 Cores with 24.0 GB of physical memory (RAM) and a 2 TB hard drive.

Six different approaches were used to cluster a set of artificially generated DNA reads. The set of artificially generated DNA reads were copied to make 20 copies of each read and then modified with 5% random error (2% substitutions; 1.5% deletions; 1.5% insertions) to simulate the effect of oligonucleotide sequencer misreads. The number of original starting reads in four different data set sizes were tested as indicated by the column "No. of Reads." The total number of reads in the data sets are 20 times the listed number: 200,000; 2,000,000; 20,000,000; and 40,000,000. The time is seconds for the computing device to cluster the reads is represented by "T." The error percentage, "E," is the percentage of clusters that were not recovered. A cluster is considered recovered, if a sub-cluster of the true cluster containing at least r reads is identified. The first error value is the percentage of non-recovered clusters for the recovery threshold r=10, and the second error value is the percentage of non-recovered clusters for r=15. Thus, E=50% for r=15 indicates that out of the 20-read clusters that could be formed only half could be formed with at least 15 reads correct reads. Blank cells in Table 1 below indicate the clusters were not determined because processing did not finish in a reasonable amount of time.

making buckets decreases accuracy. Adding the signature approach described above further reduces time, but does not affect accuracy.

"LSH" stands for locality-sensitive hashing, which is the hashing technique disclosed above. In this example the hash length is 10, q=10. The "LSE 70" approach iterates through the process of creating buckets and computing clusters 70 times. "LSE 250" iterates 250 times. Both LSH 70 and LSH 250 are slower than "Prefix 4+Sgn." However, accuracy is increased several fold. LSH 250 is both slower and more accurate than LSH 70. Thus, the LSE approaches result in clustering that is more accurate that the prefix 4 approaches and much faster than the brute force approach.

Illustrative Sequencing Technology

The polynucleotide sequencer 112 may be implemented using any of the following sequencing technologies or another technology besides those specifically mentioned here.

A sequencing technology that can be used is sequencing-by-synthesis (Illumina® sequencing). Sequencing by synthesis is based on amplification of DNA on a solid surface using fold-back PCR and anchored primers. The DNA is fragmented, and adapters are added to the 5'- and 3'-ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluo-

TABLE 1

Clustering by Edit Distance

| No. of Distinct Reads | Brute Force | Brute Force + Sgn | Prefix 4 | Prefix 4 + Sgn | LSH 70 | LSH 250 |
|---|---|---|---|---|---|---|
| 10,000 | T: 8,200 | T: 25 | T: 3 | T: 1 | T: 2 | T: 3 |
|  | E: 0% | E: 0% | E: 1.8%, 59% | E: 1.8%, 59% | E: 0.1%, 9.3% | E: 0%, 0.3% |
| 100,000 |  | T: 3,450 | T: 74 | T: 8 | T: 16 | T: 32 |
|  |  | E: 0% | E: 1.8%, 58% | E: 1.8%, 58% | E: 0.3%, 12% | E: 0%, 0.6% |
| 1,000,000 |  |  | T: 6,017 | T: 90 | T: 180 | T: 370 |
|  |  |  | E: 1.7%, 58% | E: 1.7%, 58% | E: 0.5%, 16% | E: 0%, 0.8% |
| 2,000,000 |  |  | T: 23,375 | T: 283 | T: 386 | T: 770 |
|  |  |  | E: 1.7%, 58% | E: 1.7%, 58% | E: 0.6%, 16% | E: 0.01%, 0.8% |

The "Brute Force" approach calculates edit distance (as described above) between each pair of reads and merges reads if the edit distance is below a threshold value. This pair-wise comparison approach requires $n^2$ calculations of edit distance, where n is the total number of reads. Brute Force is accurate but slow. "Sgn" indicates that signatures were calculated for all reads (as described above) and a Hamming distance between signatures was used for clustering when the Hamming distance was either below a first threshold or above a second threshold. Brute Force+Sgn is accurate and much faster than Brute Force alone.

"Prefix 4" uses a four-character prefix of the reads to first group the reads into buckets then clusters are formed in the buckets by pair-wise comparison of edit distances. Grouping into buckets reduces the processing time, but this basis for rophores, and an image is captured and the identity of the first base is recorded. The 3' terminators and fluorophores from each incorporated base are removed and the incorporation, detection, and identification steps are repeated.

Another example of a sequencing technique that can be used is nanopore sequencing. A nanopore is a small hole of the order of 1 nanometer in diameter. Immersion of a nanopore in a conducting fluid and application of a potential across the nanopore results in a slight electrical current due to conduction of ions through the nanopore. The amount of current that flows through the nanopore is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technology that can be used includes the single molecule, real-time (SMRT™) technology of Pacific Biosciences. In SMRT™, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure that enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another sequencing technique that can be used is Helicos True Single Molecule Sequencing (tSMS). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm². The flow cell is then loaded into an instrument, e.g., a HeliScope™ sequencer, and a laser illuminates the surface of the flow cell, revealing the position of each template. A CCD camera can map the position of the templates on the flow cell surface. The template fluorescent-label is then cleaved and washed away. The sequencing reaction begins by introducing a DNA polymerase and a fluorescently-labeled nucleotide. The oligo-T nucleic acid serves as a primer. The polymerase incorporates the labeled nucleotides to the primer in a template-directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently-labeled nucleotides until the desired read length is achieved. Sequence information is collected with each nucleotide addition step.

Another example of a DNA sequencing technique that can be used is SOLiD™ technology (Applied Biosystems). In SOLiD™ sequencing, DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, templates, and PCR components. Following PCR, the templates are denatured and beads are enriched to separate the beads with extended templates. Templates on the selected beads are subjected to a 3' modification that permits bonding to a glass slide.

Another example of a sequencing technique that can be used involves using a chemical-sensitive field effect transistor (chemFET) array to sequence DNA. In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an ion-sensitive field effect transistor (ISFET) to sequence DNA. Ion Torrent™ sequencing is an example of this technique. In this technique, no labelling molecules are necessary and during DNA synthesis incorporation of each nucleotide is detected. In succession, either adenine, cytosine, guanine, or thymine is flowed through the DNA chamber, and if a nucleotide becomes incorporates into the nascent strand, the reaction emits a hydrogen ion. The hydrogen ion emission is detected, and this indicates which based became incorporated at a given position.

Another example of a sequencing technique that can be used involves using an electron microscope. In one example of the technique, individual DNA molecules are labeled using metallic labels that are distinguishable using an electron microscope. These molecules are then stretched on a flat surface and imaged using an electron microscope to measure sequences.

All technologies for sequencing DNA are associated with some level of error and the type and frequency of errors differs by sequencing technology. For example, sequencing-by-synthesis creates an error in about 2% of the base calls. A majority of these errors are substitution errors. Nanopore sequencing has a much higher error rate of about 15 to 40% and most of the errors caused by this sequencing technology are deletions. The error profile of a specific sequencing technology may describe the overall frequency of errors as well as the relative frequency of various types of errors.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A system comprising:
at least one processing unit;
a memory in communication with the processing unit; and
a clusterization module stored in the memory and executable on the processing unit to divide a plurality of DNA reads into clusters based at least in part on (i) signatures that deterministically embed edit-distance space into Hamming space and (ii) a randomized locality-sensitive hashing (LSH).

Clause 2. The system of clause 1, wherein the at least one processing unit comprises a central processing unit (CPU) with Same Instruction Multiple Data (SIMD) or Single Program Multiple Data (SPMD) architecture.

Clause 3. The system of clause 1-2, wherein the clusterization module comprises an edit distance module stored in the memory and executable on the processing unit to calculate an edit distance between a first read of the plurality of DNA reads and a second read of the plurality of DNA reads based on a minimum number of insertions, deletions, and substitutions that change the first read of the plurality of DNA reads into the second read of the plurality of DNA reads.

Clause 4. The system of clause 1-3, wherein the clusterization module comprises a hash module that determines the randomized LSH based at least in part on (i) a random permutation of numbers and wherein the signatures comprise binary signatures or (ii) nucleotides adjacent to an occurrence of a randomly selected string within a DNA read.

Clause 5. The system of clause 4, wherein the clusterization module comprises a bucket module that groups DNA reads having a same hash into a same bucket.

Clause 6. The system of clause 5, wherein the clusterization module comprises a partition module that assigns two DNA reads in the same bucket to a same cluster based at least in part on a difference in the Hamming space between the two DNA reads being less than a threshold distance.

Clause 7. The system of clause 1-6, further comprising a signature module stored in the memory and executable on the processing unit to:
find k-grams for the plurality of DNA reads;
encode the k-grams as bit strings; and
concatenate the bit strings into signatures.

Clause 8. The system of clause 1-7, further comprising a device interface configured to receive the plurality of DNA reads from a polynucleotide sequencer.

Clause 9. A method comprising:
receiving a plurality of reads from a polynucleotide sequencer;
computing a signature for a first read from the plurality of reads, the signature being a bit string generated in part by a set of k-grams within the first read;
generating a hash for the first read, the hash based at least in part on a sequence of the first read;
grouping the first read with a second read having a same hash into a same bucket;
computing an edit distance between the first read and the second read;
determining that the edit distance is below a threshold value; and
merging a first cluster containing the first read with a second cluster containing the second read into a third cluster.

Clause 10. The method of clause 9, wherein the plurality of reads includes more than a billion reads representing more than a million different DNA strands.

Clause 11. The method of clause 9-10, wherein computing the signature comprises:
dividing the first read into two or more sub-reads;
finding all k-grams for each of the two or more sub-reads;
encoding the k-grams as bit strings; and
concatenating the bit strings into the signature.

Clause 12. The method of clause 9-11, wherein generating the hash comprises:
generating a string of random numbers;
assigning a different random number from the string of random numbers to individual bits in at least a portion of the signature; and
setting the hash as a subset of the string of random numbers that are assigned to the individual bits.

Clause 13. The method of clause 12, further comprising selecting the individual bits based on bit value.

Clause 14. The method of clause 9-11, wherein generating the hash comprises:
generating a string of random nucleotides;
identifying an occurrence of the string of random nucleotides in the first read; and
setting the hash as a sequence of nucleotides adjacent to the occurrence of the string of random nucleotides in the first read.

Clause 15. The method of clause 9-14, wherein computing the edit distance comprises counting a minimum number of insertions, deletions, and substitutions that change the first read into the second read.

Clause 16. The method of clause 9-15, wherein determining that the edit distance is below a threshold value comprises determining that a signature distance between the signature for the first read and a signature for the second read is below a signature distance threshold.

Clause 17. The method of clause 16, wherein the signature distance is a Hamming distance.

Clause 18. The method of clause 9-17, further comprising:
marking the first read as a representative read for the third cluster;
identifying the representative read and a third read within a fourth cluster in the same bucket as having a second edit distance below the threshold value; and
merging the third cluster containing the representative read with the fourth cluster including the third read.

Clause 19. A method comprising:
separating a plurality of DNA reads into a plurality of buckets; and
clustering DNA reads in one of the plurality of buckets into clusters based at least in part on edit distance between respective pairs of the DNA reads.

Clause 20. The method of clause 19, wherein separating the plurality of DNA reads into the plurality of buckets is based at least in part on prefixes of the plurality of DNA reads.

Clause 21. The method of clause 19-20, wherein separating the plurality of DNA reads into the plurality of buckets is based at least in part on hashes of the plurality of DNA reads.

Clause 22. The method of clause 21, wherein a hash for a one of the plurality of DNA reads is based at least in part on a binary signature of the one of the plurality of DNA reads and a random permutation of numbers.

Clause 23. The method of clause 19-22, wherein the edit distance is calculated by a minimum number of insertions, deletions, and substitutions to transform a first DNA read into a second DNA read.

Clause 24. The method of clause 19-23, wherein the edit distance is approximated by a Hamming distance between a binary signature of a first DNA read of the plurality of DNA reads and a binary signature of a second DNA read of the plurality of DNA reads.

Clause 25. The method of clause 24, further comprising:
determining that the Hamming distance is less than a first threshold; and placing the first DNA read of the plurality of DNA reads and the second DNA read of the plurality of DNA reads in a same cluster.

Clause 26. The method of clause 24, further comprising:
determining that the Hamming distance is greater than a second threshold; and
placing the first DNA read of the plurality of DNA reads and the second DNA read of the plurality of DNA reads in different clusters.

Clause 27. The method of clause 24, further comprising:
determining that the Hamming distance is between a first threshold and a second threshold;
calculating the edit distance for the first DNA read of the plurality of DNA reads and the second DNA read of the plurality of DNA reads;
determining that the edit distance is less than an edit-distance threshold; and placing the first DNA read of the plurality of DNA reads and the second DNA read of the plurality of DNA reads in a same cluster.

Clause 28. Computer-readable media encoding instructions which when executed by a processing unit cause a computing device to perform the method of any of clauses 9-27.

Clause 29. A system comprising one or more processing units and memory configured to implement the method of any of clauses 9-27.

Clause 30. A system comprising:
at least one processing unit;
a memory in communication with the processing unit;
means for dividing a plurality of DNA reads into clusters based at least in part on (i) signatures that deterministically embed edit-distance space into Hamming space and (ii) a randomized locality-sensitive hashing (LSH);
means for calculating an edit distance between a first read of the plurality of DNA reads and a second read of the plurality of DNA reads based on a minimum number of insertions, deletions, and substitutions that change the first read of the plurality of DNA reads into the second read of the plurality of DNA reads;
means for determining the randomized LSH based at least in part on (i) a random permutation of numbers and wherein the signatures comprise binary signatures or (ii) nucleotides adjacent to an occurrence of a randomly selected string within a DNA read; and
means for signing two DNA reads in the same bucket to a same cluster based at least in part on a difference in the Hamming space between the two DNA reads being less than a threshold distance.

Conclusion

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

The invention claimed is:

1. A system for improving accuracy of polynucleotide sequencing, the system comprising:
a polynucleotide sequencer configured to generate a plurality of DNA reads from a plurality of DNA strands having different nucleotide sequences, wherein the plurality of DNA reads includes errors introduced by the polynucleotide sequencer;
at least one processing unit;
a memory in communication with the processing unit;
a clusterization module stored in the memory and executable on the processing unit to divide the plurality of DNA reads into clusters by first grouping DNA reads having a same hash as determined by randomized locality-sensitive hashing (LSH) into buckets and then grouping DNA reads in a same bucket into clusters based at least in part on similarity of signatures of the DNA reads, wherein the signatures are generated by a technique that deterministically embeds edit-distance space into Hamming space; and
a consensus output sequence generator stored in the memory and executable on the processing unit configured to generate a single consensus output sequence from each cluster that has less error than individual reads in each cluster.

2. The system of claim 1, wherein the clusterization module comprises an edit distance module stored in the memory and executable on the processing unit to calculate an edit distance between a first read of the plurality of DNA reads and a second read of the plurality of DNA reads based on a minimum number of insertions, deletions, and substitutions that change the first read of the plurality of DNA reads into the second read of the plurality of DNA reads.

3. The system of claim 1, wherein the clusterization module comprises a hash module that determines the randomized LSH based at least in part on a random permutation of numbers and wherein the signatures comprise binary signatures.

4. The system of claim 1, further comprising a signature module stored in the memory and executable on the processing unit to:
split a one of the plurality of DNA reads into sub-reads;
find k-grams for the sub-reads of the plurality of DNA reads;
encode the k-grams as bit strings based on comparison to a comparison string that includes all possible substrings of length k; and
concatenate the bit strings into signatures.

5. The system of claim 1, wherein the plurality of DNA reads comprises over 200,000 reads.

6. The system of claim 1, further comprising a device interface configured to receive the plurality of DNA reads from the polynucleotide sequencer.

7. The system of claim 1, wherein the clusterization module comprises a hash module that determines the randomized LSH based at least in part on nucleotides adjacent to an occurrence of a randomly selected anchor string within a DNA read.

8. The system of claim 1, wherein the clusterization module comprises a partition module that assigns two DNA reads in the same bucket to a same cluster based at least in part on a difference in the Hamming space between the two DNA reads being less than a threshold distance.

9. The system of claim 1, wherein the at least one processing unit comprises a central processing unit (CPU) with Same Instruction Multiple Data (SIMD) or Single Program Multiple Data (SPMD) architecture.

10. The system of claim 1, wherein the at least one processing unit comprises a multicore processing system and all DNA reads grouped into a same bucket are processed by a single core of the multicore processing system for the grouping DNA reads into clusters.

11. The system of claim 1, wherein a hash length of the LSH is 10.

12. The system of claim 1, wherein the clustering module iteratively groups the DNA reads into buckets and into clusters and the process of creating buckets and computing clusters is repeated iteratively about 250 times.

13. The system of claim 1, wherein over 99% of the clusters are accurately formed as determined by inclusion at least three quarters of the DNA reads of a DNA strand in a same cluster.

14. The system of claim 1, wherein the plurality of DNA strands comprises multiple copies of each of the individual ones of the plurality of DNA strands in a DNA sample pool.

15. The system of claim 1, wherein the plurality of DNA strands comprises artificially synthesized DNA that encode digital information.

16. The system of claim 15, further comprising a converter stored in the memory and executable on the processing unit to convert the single consensus output sequence into binary data thereby retrieving the digital information.

* * * * *